Nov. 14, 1967 D. B. LOWRY Plant Pat. 2,776
NECTARINE TREE
Filed Feb. 21, 1966
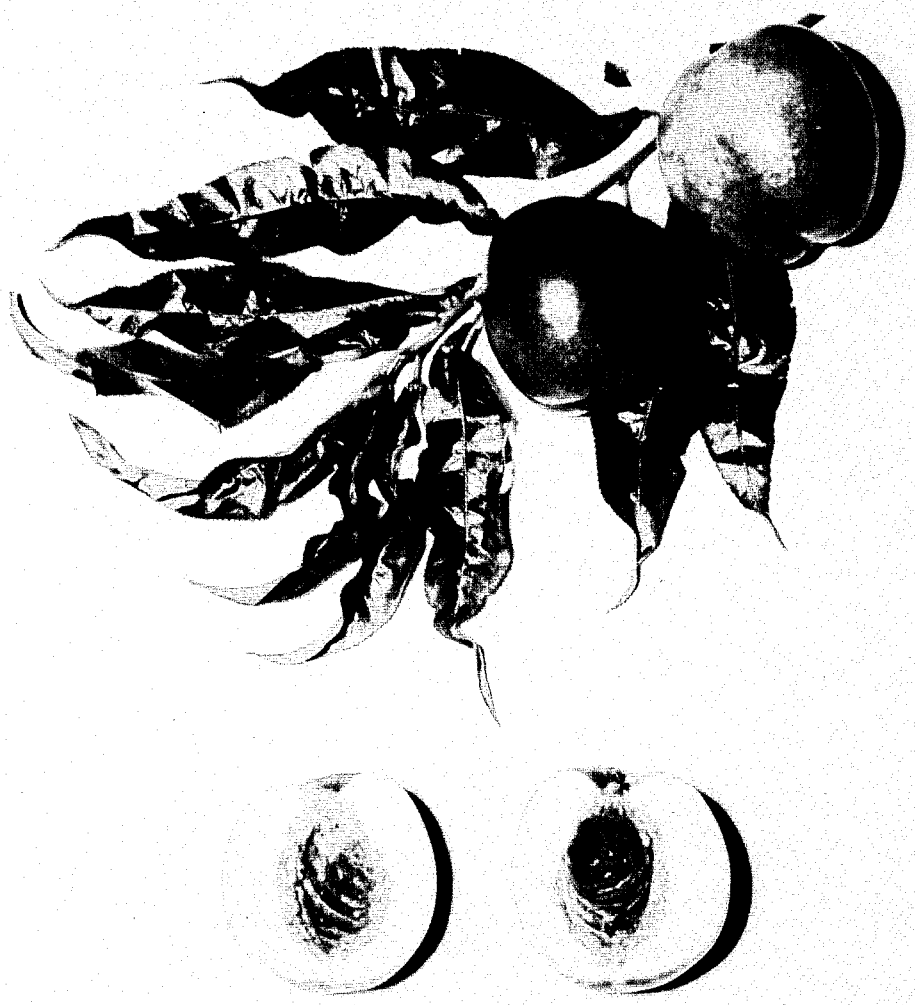
INVENTOR
David B. Lowry
BY
Webster & Webster
ATTORNEYS

United States Patent Office

Plant Pat. 2,776
Patented Nov. 14, 1967

2,776

NECTARINE TREE

David B. Lowry, P.O. Box 464,
Medford, Oreg. 97501

Filed Feb. 21, 1966, Ser. No. 529,162
1 Claim. (Cl. Plt.—41)

This invention relates to a new and distinct variety of nectarine tree which is a regular and productive bearer of medium size, yellow flesh, freestone fruit having orange-yellow skin substantially overspread with red. The fruit harvests in mid-season and is of especially desirable commercial quality.

In comparison to other mid-season nectarines, and particularly the Sun Grand (United States Plant Patent No. 974), the fruit of the present variety—which is bright in color and uniform in appearance—is distinctively characterized by quite firm flesh when fully ripe; this resulting in superior shipping quality and assuring of a longer shelf life. The fruit is further characterized by thin skin which is extremely smooth and highly waxed, both tending to prevent the occurrence of brown rot and decay; a yellow ground color which shades more to orange and is overspread with a more diffused red having distinct spotting; a seed which is smaller in size so that there is more flesh and less waste; and a mild flavor which is less acid and not as sweet, but distinctive and pleasant.

Additionally, the fruit of the present variety is exceptionally free of common growth defects such as skin cracks, split pits, and doubles.

Further, the present variety withstands relatively low temperatures or frost; the tree having been undamaged by 0° F. while the blossoms have withstood 27° F.

Still further, the tree of the present variety is open and spreading; being characterized by fruiting branches which are less rigid and not as upright as those of the Sun Grand.

I originated the herein claimed variety of nectarine tree on an orchard located near Talent, Oreg.; the variety being a first generation cross between the Fireglobe (unpatented) and the Sun Grand nectarines as the seed and pollen parents, respectively. Seed from such cross was planted, and the resultant seedlings were brought into bearing under continuing and careful observation. One such seedling—and which is the instant variety—was recognized by me as being of exceptional merit and hence I selected it for propagation.

Subsequent to origination of the variety and recognition by me of its novel characteristics and commercial potential, I asexually reproduced it by budding on seedling Merrill Splendor (United States Plant Patent No. 1,257) peach trees on another orchard, also located near Talent, Oreg. Such asexual reproductions of the variety, in careful comparison with the original or parent tree, were found to run true in all respects.

The drawing is an illustration, by photographic reproduction in color, of a twig with leaves and fruit; a separate fruit being shown as cut in half to expose the flesh and with the stone remaining in one half.

Referring now more specifically to the pomological details of this new and distinct variety of nectarine tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Vigorous.

Tree—Continued
- *Growth.*—Spreading.
- *Density.*—Open.
- *Form.*—Vase shaped.
- *Hardiness.*—Hardy.
- *Production.*—Productive.
- *Bearing.*—Regular bearer.

Branches:
- *Form.*—Medium.
- *Texture.*—Medium.
- *Color.*—Dull brown.
- *Lenticels.*—Number—few. Size—medium.

Leaves:
- *Size.*—Medium. Average length—5". Average width—1½".
- *Form.*—Oval; acuminate.
- *Thickness.*—Medium.
- *Texture.*—Smooth.
- *Margin.*—Crenate.
- *Petiole.*—Medium length; medium thickness.
- *Glands.*—Average number—5. Opposite; medium size; reniform; green. Position—basal and on petiole.
- *Stipules.*—Terminal; deciduous.
- *Color.*—Top side—medium green (23–L–7). Under side—lighter green (22–L–7).

Flower buds:
- *Hardiness.*—Hardy.
- *Size.*—Medium.
- *Length.*—Medium.
- *Form.*—Plump; free.

Flowers:
- *Blooming period.*—Average date of first bloom—April 1st. Average date of full bloom—April 10th; medium, as compared with other varieties.
- *Size.*—Medium.
- *Color.*—Pink.

Fruit:
- *Maturity when described.*—Eating ripe—Sept. 3, 1965.
- *Average date of first picking.*—September 1st.
- *Average date of last picking.*—September 15th.
- *Size.*—Uniform; medium. Average diameter axially—2 3/10" to 2 3/5". Average transversely in suture plane—2 2/5" to 2 7/10".
- *Form.*—Uniform; unsymmetrical; globose; compressed toward suture.
- *Suture.*—Distinct; deep; marked depression beyond pistil point.
- *Ventral surface.*—Strongly lipped throughout both sides.
- *Lips.*—Unequal.
- *Cavity.*—Abrupt; elongated in suture plane with suture showing on one side. Average depth—7/16". Average breadth—⅝".
- *Markings.*—Broad to narrow dark red band.
- *Base.*—Rounded.
- *Apex.*—Depressed.
- *Pistil point.*—Apical.

Skin:
- *Thickness.*—Thin.
- *Texture.*—Medium.
- *Flavor.*—Slightly bitter.
- *Tenacity.*—Tenacious to flesh.
- *Tendency to crack.*—None.
- *Down.*—Wanting.
- *Color.*—Orange-yellow (11–L–7) substantially overspread with a diffused red (5–L–5 to 6–L–7), with distinct spotting.

Flesh:

*Juice.*—Moderate; rich.
*Texture.*—Firm; fine; meaty.
*Fibers.*—Few; fine; tender.
*Ripens.*—Evenly; earliest along both lips.
*Flavor.*—Mild.
*Aroma.*—Distinct.
*Eating quality.*—Good.
*Color.*—Yellow (11–L–4 to 11–L–5). Surface of pit cavity—pink.

Stone:

*Type.*—Free; parts from flesh smoothly.
*Fibers.*—Short.
*Size.* — Small. Average length — 1⅜". Average breadth—1". Average thickness—¾".
*Form.*—Oval.
*Base.*—Oblique.
*Hilum.*—Oval.
*Apex.*—Acute.
*Sides.*—Unequal; curved on right or left side.
*Surface.*—Irregularly furrowed toward apex; ridged toward apex from base to above center.
*Ridges.*—Rounded toward apex; interrupted.
*Pits.*—Elongated.
*Ventral edge.*—Thin, without wing.
*Dorsal edge.*—Narrow, with narrow groove to above center.

Stone—Continued

*Tendency to split.*—None.
*Color.*—Brown, tinged with red (7–J–6).

Use: Dessert.
Keeping quality: Superior.
Resistance to insects and diseases: Good.
Shipping quality: Superior.

The nectarine tree and its fruit herein described may vary in slight detail due to climatic and soil conditions under which the variety may be grown; the present description being of the variety as grown near Talent, Oreg.

The following is claimed:

A new and distinct variety of nectarine tree, substantially as illustrated and described, essentially characterized—particularly in comparison to the Sun Grand—by the regular and productive bearing of uniform, medium size, freestone fruit having yellow flesh quite firm when fully ripe; thin, smooth, highly waxed skin of yellow ground color shading more to orange and substantially overspread with a diffused red having distinct spotting; a smaller seed; and a mild flavor which is less acid and not as sweet.

No references cited.

ROBERT E. BAGWILL, *Primary Examiner.*